(12) United States Patent
Landschuetz et al.

(10) Patent No.: US 8,519,706 B2
(45) Date of Patent: Aug. 27, 2013

(54) METHOD AND MAGNETIC RESONANCE TOMOGRAPHY APPARATUS FOR TRIGGERED ACQUISITION OF MAGNETIC RESONANCE DATA

(75) Inventors: Wilfried Landschuetz, Baiersdorf (DE); Michaela Schmidt, Uttenreuth (DE); Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 623 days.

(21) Appl. No.: 12/770,887

(22) Filed: Apr. 30, 2010

(65) Prior Publication Data

US 2010/0277173 A1    Nov. 4, 2010

(30) Foreign Application Priority Data

Apr. 30, 2009 (DE) .......................... 10 2009 019 592

(51) Int. Cl.
*G01V 3/00* (2006.01)
(52) U.S. Cl.
USPC ........................... 324/306; 324/309; 600/413
(58) Field of Classification Search
USPC .................. 324/306, 307, 309; 600/407, 413
See application file for complete search history.

(56) References Cited

U.S. PATENT DOCUMENTS

| 4,777,957 | A | * | 10/1988 | Wehrli et al. | 600/413 |
|---|---|---|---|---|---|
| 5,251,628 | A | * | 10/1993 | Foo | 600/413 |
| 5,908,386 | A | | 6/1999 | Ugurbil et al. | |
| 5,997,883 | A | * | 12/1999 | Epstein et al. | 324/306 |
| 6,032,069 | A | * | 2/2000 | Elgavish et al. | 600/413 |
| 6,618,605 | B1 | * | 9/2003 | Wolff et al. | 600/410 |
| 7,308,299 | B2 | * | 12/2007 | Burrell et al. | 600/428 |
| 2004/0049106 | A1 | | 3/2004 | Kanazawa | |
| 2006/0100503 | A1 | | 5/2006 | Takai et al. | |
| 2008/0021304 | A1 | | 1/2008 | Stemmer | |
| 2008/0242973 | A1 | | 10/2008 | Warmuth | |

FOREIGN PATENT DOCUMENTS

DE    102005034686 A1    2/2007

OTHER PUBLICATIONS

Stemmer et al., "GRAPPA-accelerated short axis BLADE EPI for multi-shot diffusion weighted imaging," Siemens AG, Healthcare Sector, Erlangen, Germany, p. 5423.

* cited by examiner

*Primary Examiner* — Louis Arana
(74) *Attorney, Agent, or Firm* — Schiff Hardin LLP

(57) ABSTRACT

In a method and magnetic resonance tomography apparatus for triggered implementation of a measurement (composed of partial measurements) in the magnetic resonance tomography apparatus, at least one image data set is determined from the data acquired within the scope of the partial measurements, and for triggering a reference point of the movement phase of the movement is used. The image data set is acquired in segments; the reference point is detected by a control device independent of a partial measurement, and the partial measurement following the detected reference point is conducted depending on the independently detected reference point. The wait time that specifies the interval from the end of the partial measurement to the beginning of the next partial measurement is adapted depending on the point in time of detection.

23 Claims, 3 Drawing Sheets

METHOD AND MAGNETIC RESONANCE TOMOGRAPHY APPARATUS FOR TRIGGERED ACQUISITION OF MAGNETIC RESONANCE DATA

BACKGROUND OF THE INVENTION

1. Field of the Invention

The present invention concerns a method for triggered implementation of a measurement composed of partial measurements in a magnetic resonance tomography apparatus, of the type wherein at least one image data set is determined from the data acquired within the scope of the partial measurements, and wherein a reference point of the movement phase of the movement is used for triggering.

2. Description of the Prior Art

For data acquisition of magnetic resonance tomography data, it is known to acquire the data in an EKG-triggered manner in order to minimize movement artifacts from the post-processed image data. The EKG signal (wherein EKG is the generally known abbreviation for electrocardiogram) is a measure of the electrical activity of the heart muscle fibers. The contraction of the heart muscle is produced by an electrical excitation, which is detected with the EKG apparatus. The EKG signal is a periodic signal and the different phases of the cardiac cycle are designated with letters. The conventional sequence is P-Q-R-S-T-U. The R-spike exhibits the greatest amplitude; it is therefore normally used as a reference point of the triggering.

The detection of the EKG signal ensues via electrodes attached to the patient. The signals detected by the electrodes are relayed via electrical lines from the magnetic resonance tomography apparatus to an EKG device. Naturally the EKG signal can be filtered or post-processed in another manner.

Furthermore, it is known to trigger measurements depending on the breathing movement. For this purpose, a sensor is provided that transduces the breathing movement into an electrical signal. This signal is a measure of the breathing movements and thus can be used to control the magnetic resonance device. Only the EKG triggering, however, is discussed in detail in the following.

The term "data acquisition" is used herein to encompass the entire measurement procedure. In contrast to the data acquisition, the time period during which actual data are stored in a storage medium is designated as measurement with data acquisition. During the magnetic resonance data acquisition, the readout gradient is typically activated for frequency coding in order to provide the measurement signal with a spatial coding during the data acquisition.

A number of differently designed magnetic resonance measurements or measurement methods are available. The terms "data acquisition" or "measurements" encompass all types of measurements. One or more two-dimensional or three-dimensional image data sets, multiple image data sets from different slices of the examination subject and data sets with and without weighting with regard to a specific parameter can be obtained as a result of the post-processing of the acquired raw data. Within the scope of the post-processing it can also be necessary to supplement the data acquired within the scope of one measurement with data of other measurements, or to have to draw on additional data from other measurements for post-processing in order to obtain one or more image data sets from the acquired data.

Such a measurement is composed of partial measurements. The partial measurements are basically of the same design; only the strength of the phase-coding gradient or of the slice gradients (and rarely also of the readout gradient) is varied in a predetermined manner. The partial measurement can include one or more preparation modules in order to weight measurement signal corresponding to a physical parameter. For example, multiple preparation modules are required if multiple image data sets from different positions of the patient are acquired and a separate preparation is required for every single one of these image data sets (known as slices).

In EKG-triggered or breathing-triggered data acquisition, a partial measurement is started after detection of the trigger signal. One or more data acquisitions can ensue in this partial measurement. These data acquisitions can belong to a single image data set, or multiple data acquisitions can belong to multiple image data sets, or multiple data acquisitions can respectively belong to a single image data set. The design and the sequence of corresponding measurements are hereby known and therefore require no detailed explanation herein.

The time span provided between two R-spikes is designated as an RR-interval. The partial measurement to be conducted in this interval includes not only the data acquisition as such but also, as described, preparation steps necessary for this in the form of magnetization preparation modules. This is discussed below in further detail.

In a known method for EKG-triggered implementation of a magnetic resonance measurement, a partial measurement is conducted after detection of an R-spike. After the end of the partial measurement, the control device of the magnetic resonance tomography apparatus communicates with the EKG device in order to be able to start the next partial measurement after displaying the next R-spike. Since the heart beat of a patient is subject to a certain variability, a safety interval from the end of the (last) partial measurement to the point in time of the expected next R-spike is typically observed (maintained) in order to be able to compensate for such fluctuations. The full RR-interval is accordingly not utilized; the RR interval beginning with this R-spike is not used to implement a partial measurement.

SUMMARY OF THE INVENTION

An object of the present invention is to provide a method for triggering a magnetic resonance measurement that allows a reliable and disruption-free data acquisition even given variable heart frequency of the patient.

This object is achieved by a method of the aforementioned type wherein, according to the invention, the image data set is acquired in segments, and the reference point is detected by a control device independently of a partial measurement, and the partial measurement following the detected reference point is conducted depending on the independently detected reference point, and wherein the wait time that specifies the interval from the end of the partial measurement to the beginning of the next partial measurement is adapted depending on the point in time of detection.

Instead of waiting for the next detection of the reference point (usually the R-spike), this is detected independently of the partial measurement. If the heart beat now accelerates, the time span of the RR-interval accordingly shortens. In spite of this shortening, however, no RR interval is skipped since the reference point is detected independently of the implementation of a partial measurement. If the reference point still occurs during a partial measurement, the beginning of the next partial measurement is accordingly delayed, meaning that the wait time is shortened.

In addition to the adaptation of the wait time, a preparation module, or multiple or different preparation modules, can also be adapted within the scope of a partial measurement. Naturally this adaptation is likewise taken into account in the calculation of the wait time. For example, the inversion time can likewise be shortened given a shortening of the wait time in a preparation module consisting of inversion pulse and inversion time.

As used herein the terms "measurement" and "partial measurement" encompass all known methods and techniques in which at least one image can be obtained from the data. The data are acquired k-space line-by-k-space line. Techniques that acquire only a portion of certain k-space lines and techniques in which not all k-space lines are acquired to obtain a complete image data set, and wherein the missing lines are supplemented by post-processing methods, are also included in the term "measurement". Such methods are known under the names partial Fourier and half Fourier methods. In a partial measurement, only one k-space line per image data set, or multiple k-space lines per image data set can be acquired. For the method according to the invention it is only necessary that at least two k-space lines are acquired within the scope of a partial measurement.

The method according to the invention produces a more robust data acquisition given an irregular heart beat. Since the detection of the R-spike ensues independently of the end of a partial measurement, RR-intervals (and therefore no cardiac cycles) are no longer skipped. In methods whose magnetization preparation achieves a certain steady state, this steady state is accordingly maintained, while the magnetization decays into an undefined state upon omitting a cardiac cycle. The measurement times of the implemented measurements can therefore furthermore be shortened, and in particular measurements during breath-hold times are implemented optimally.

In the following it is assumed that at least two image data sets are determined from the data.

The number of image data sets to be acquired during a partial measurement can advantageously be determined depending on the time interval of at least two of the last acquired reference points. In the event that the heart beat of the patient accelerates overall and is not just irregular, it can occur that the time interval required by the partial measurement is longer than the provided RR-interval. In this case the acceleration of the heart beat must be detected, and possibly the duration of the partial measurement (in the form of the number of image data sets to be acquired, i.e. k-space lines) must be adapted. A fundamental reduction of the number of k-space lines to be acquired is naturally only applied if a non-transient reduction of the RR-interval is assumed. In the consideration of the last two detected reference points, the duration of the time interval defined by them can be established. If this interval is shorter than the time interval required for the data acquisition, the number of k-space lines to be acquired is thus to be reduced since otherwise—in spite of shortening of the wait time—portions of cardiac cycles must be skipped. An adaptive adaptation to an accelerated heart beat is achieved via this embodiment. Naturally, an adaptation to a slowed heart beat can also be hereby achieved, but slowing of the heart beat is normally not a problem in a measurement.

The missing data from image data sets that are not acquired due to the adaptation of the time interval can be particularly supplemented with data of at least one of the reference image data sets. In magnetic resonance tomography examinations, both morphological and functional image data are regularly acquired in the form of experiments. The morphological image data sets show more or less the spin density distribution in the examination region of the patient while the functional image data are relaxation time-weighted, flow-weighted or even perfusion-weighted. A quantification of the corresponding variable (for example T1, perfusion or diffusion) can also be achieved with at least two image data sets weighted according to a specific physical variable. The morphological and functional image data can thereby corresponding with regard to parameters to be set, such as field of view, number of image elements, slice thickness etc. It is accordingly possible to make use of morphological image data sets or individual k-space lines of these to complete incompletely acquired functional image data sets. Alternatively, it is also conceivable to use corresponding k-space lines of a functional image data set that was acquired at a different point in time of the cardiac phase or in another slice to complete an incompletely acquired image data set. Appropriate methods to complete incomplete image data sets and the corresponding respective requirements are well known to those skilled in the art.

In addition to the general method described above, a need exists to additionally or alternatively improve the prior art for perfusion measurements.

A perfusion measurement as used herein is the measurement of a non-periodical process in which the data acquisition allows signal change in the blood due to a contrast agent to be tracked over time. Perfusion measurements are thus primarily relaxation-weighted measurements. For example, perfusion information exists in the time curve of the signal intensity of a pixel. Quantitative perfusion values can be acquired from the acquired data with the aid of model assumptions.

A method of the aforementioned type provides an alternative solution to the problem according to the invention in the implementation of a perfusion measurement, wherein at least two image data sets are acquired, from which image data sets at least one item of perfusion information is determined, and wherein the image data sets depict different points of the examination subject, and the reference point is detected by a control device, independently of a partial measurement, and the partial measurement is terminated in the event of a reference point being detected before the end of the partial measurement, after a defined time span after detection of the reference point.

Specifically in perfusion measurements the problem occurs that—due to the magnetization preparation to be conducted and the number of slices to be acquired—only a small wait time, or no wait time at all, is available for adaptation to a detected reference point. If the available wait time is not sufficient, additional room to adjust must be provided in a perfusion measurement. This room to adjust is achieved by terminating a partial measurement of a perfusion measurement depending on additional parameters in order to begin the next partial measurement (thus the preparation and acquisition of the next k-space lines of the image data sets to be acquired) promptly after detection of the R-spike or of the reference point.

This possibility results from the fact that the slices or image data sets to be acquired in different slices are not all equally relevant; rather, some slices have a greater significance than others. Moreover, the omission of RR-intervals is serious, particularly in perfusion measurements, since in total only a few RR-intervals are available for measurement (for example in "first pass" measurements), and the data evaluation becomes difficult to impossible given the omission of one or even more RR-intervals. This omission can lead to an incorrect quantification of the perfusion values. Therefore, avoiding the non-omission of an RR-interval is particularly important in perfusion measurements.

By prompt termination of a partial measurement it is thus guaranteed that every provided RR-interval is used. For example, the perfusion of a contrast agent can be completely detected. The steady state generated by an inversion pulse (for example) can also be maintained.

In addition to the maximization of the slices to be acquired, and therefore of the slice coverage, the method therefore also allows an automatic adaptation of the slice coverage. The slice coverage specifies the volume, or in cross-section the area, of the tissue acquired by the magnetic resonance measurement, which directly represents a measure of the number of the acquired slices based on known size ratios. In a perfusion measurement, one or more unsegmented image data sets are thus acquired in an RR-interval or, respectively, within the scope of a partial measurement.

The time span can advantageously be set to a value of 0. A partial measurement is accordingly terminated immediately after detection of the reference point. This allows the immediate beginning of the next partial measurement. Naturally, here multiple k-space lines per image data set can also be acquired in every RR-interval, or only a single line per image data set. This depends on the implemented measurement and the respective user settings. K-space lines that have been only partially acquired are discarded, except when this is intended in specific methods (such as the aforementioned half Fourier method).

The time span can advantageously be determined depending on the ending of the data acquisition of the image data set acquired during the detection of the reference point. This means that the partial measurement is not interrupted immediately, but rather that at least the currently measured k-space line is completely acquired, and only after this is the partial measurement terminated. The data acquisition of a k-space line shifts in the range from 1-2 ms and is therefore markedly shorter than the additional steps necessary for data acquisition, for example preparation by an inversion pulse. Accordingly, the ending of the actual data acquisition of the currently acquired k-space line is normally less time-critical, which is why the acquisition of these data is still conducted.

The time span can be determined depending on the complete data acquisition of a specific number of image data sets. This guarantees that a minimum number of image data sets— and therefore of slice images—exists that the user considers to be necessary for the diagnostic finding. If the heart beat accelerates, for example, such that only a single slice is acquired per RR-interval, this could lead to a significant limitation of the significance of the acquired data. It is therefore reasonable to give the user the possibility to allow a minimum number of image data sets or, respectively, slices to be acquired in order to acquire the data set that the user requires.

The independent detection of the reference point can advantageously be started after an established time duration after the beginning of a partial measurement. The time duration can be determined depending on the end of the complete data acquisition of a specific number of image data sets. If a specific number of image data sets (for example three) is to be acquired in each case, it is not reasonable to implement an inconsequential detection of the reference point (so to speak) during the preparation and data acquisition of these image data sets. In this case the computation time resources are better conserved. The detection of the reference point then begins with the beginning of the preparation or data acquisition of an image data set whose acquisition is not mandatory.

Even when conducting perfusion measurements, the determination of the number of image data sets to be acquired advantageously ensues depending on the time interval of at least two of the last detected reference points. As already described, this procedure allows an adaptive adaptation to the accelerated heart beat. A threshold that cannot be fallen below can be particularly advantageously provided for the number of image data sets. The user can thus start with an arbitrarily high number of image data sets to be acquired; the partial measurements or the number of image data sets to be acquired are/is automatically adapted to the provided time span between the detected reference points (thus the RR-interval). A required minimum number of image data sets or slices are maintained. Complicated adaptations before the actual measurement thus are not necessary, so the residence time of the patient in the magnetic resonance tomography apparatus is shortened. If one considers that the actual measurement or, respectively, the measurement time often accounts for half of the time during which the patient is located within the magnetic resonance tomography apparatus, this type of EKG triggering entails a doubled savings potential with regard to the residence time of the patient. Moreover, setting up the measurement—thus the adjustment of the acquisition parameters—takes place faster. Additionally, the duration of the measurement as such can also be reduced to a minimum by the utilization of every occurring RR-interval. The total residence duration of the patient in the magnetic resonance tomography apparatus can thus be significantly shortened. Moreover, operating errors can be avoided.

The missing data of image data sets that were not completely acquired due to the reduction of the image data sets to be acquired can advantageously be supplemented by means of data of at least one reference image data set. This means that missing k-space lines are transferred from another data set, but not that incompletely acquired k-space lines are completed. The discussion above with regard to the reference image data sets also apply to the perfusion measurements.

Independently of whether the wait time is shortened or the partial measurement is terminated within the scope of the triggered data acquisition, the following embodiments can be provided.

A reference point is not taken into account when the time interval from the preceding reference point falls below a specific threshold. Apart from the acceleration of the heart beat, there is also the possibility of arrhythmias or also faulty triggerings. An arrhythmia is a disruption of the heart rhythm that is caused by irregularities in the excitation formation in the heart muscle. Its occurrence or the length of the heart rhythm is overlaid with a random component that is not accessible to an adaptation. The same applies for incorrect triggerings when, for example, a random signal fluctuation is confused for the reference point. Since an accelerated heart beat is not necessarily highly visible and proceeds unexpectedly, in particular given positioning of the patient in a recumbent position under administration of medicine, it is therefore reasonable to observe a minimum time interval from the preceding reference point. Previously occurring reference points are ignored as incorrect triggering.

A point in time of the cardiac phase can advantageously be used to trigger an EKG signal and as a reference point.

The R-spike can particularly advantageously be used as a reference point. This exhibits the largest signal intensity in the EKG signal and is therefore regularly used for triggering in magnetic resonance measurements. However, the methods according to the invention are not limited to the use of the R-spike; rather, in principle any phase of the heart beat can be used as a reference point.

Alternatively, a breathing signal can be used for triggering.

DESCRIPTION OF THE PREFERRED
EMBODIMENTS

Figure 1:
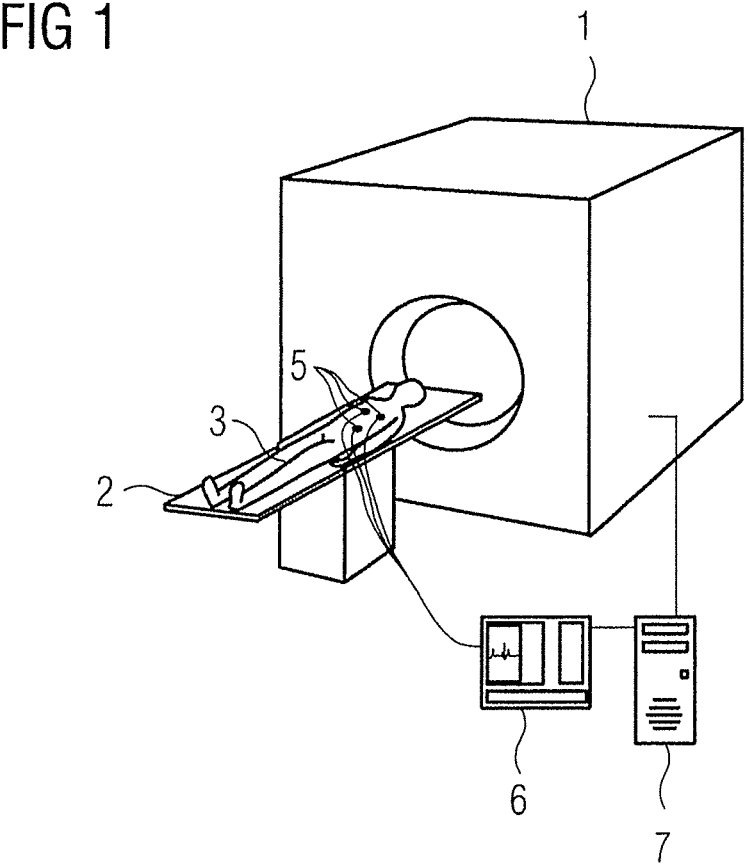
FIG. 1 schematically illustrates a magnetic resonance tomography apparatus.

FIG. 1 shows a magnetic resonance system 1 having a bore in which a patient bed 2 can be inserted. To acquire magnetic resonance data from a patient 3, the patient 3 is supported on the patient bed 2 and electrodes 5 are located on the body of the patient 3 to detect an EKG signal 4. The signals detected by the electrodes 5 are relayed to the EKG device 6. The EKG device 6 communicates with the control device 7 of the magnetic resonance system 1, wherein the EKG device 6 and the control device 6 can naturally be spatially separated devices or can also be arranged in a single housing.

Figure 2:
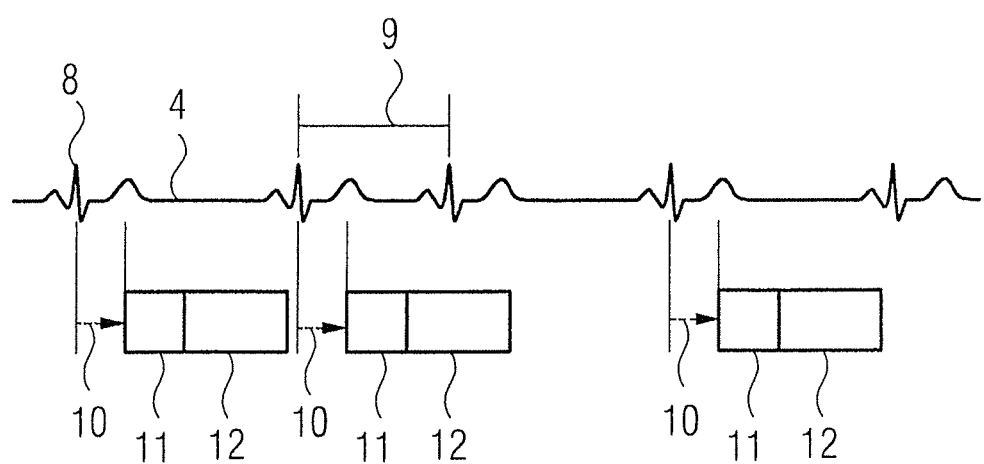
FIG. 2 shows EKG-triggered implementation of a measurement.

FIG. 2 shows a known method from the prior art for EKG-triggered implementation of a measurement. The R-spike 8 of the EKG signal 4 is used as a reference point of the cardiac phase. The time between the occurrence of two R-spikes 8 is designated as an RR-interval 9. The control device 7 of the magnetic resonance system 1 polls the trigger signal in the EKG device 6. If this occurs, a partial measurement is started. Again, this itself consists of multiple parts, namely a time interval 10, a preparation module 11 and an image data acquisition module 12. Via the time interval 10 with which the magnetization preparation is separated from the occurrence of the R-spike 8 it should be ensured that the magnetization preparation and the data acquisition always ensue in the same cardiac phase. On the other hand, via corresponding selection of the time interval 10 it is achieved that this occurs in the diastole in which the heart movement is minimal. After the end of the image data acquisition module 12, the control device 7 again polls the trigger signal in the EKG device 6. However, it can thereby occur that—due to a slight irregularity or acceleration of the heart beat—the next R-spike 8 already occurs during the partial measurement within the scope of the image data acquisition module 12. In this case a cardiac phase (in which no magnetization preparation and also no image data acquisition or, respectively, data acquisition occur) is omitted.

Figure 3:
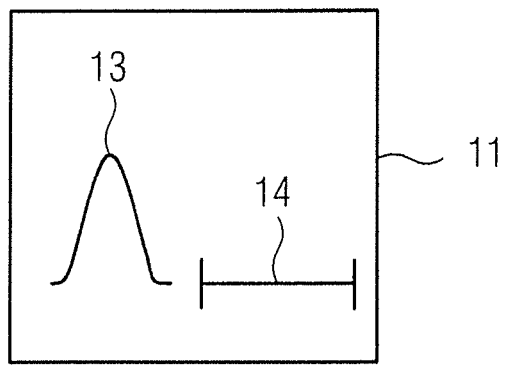
FIG. 3 shows a preparation module.

FIG. 3 shows by way of example a preparation module 11 that consists of an inversion pulse 13 and a time interval 14. The magnetization is rotated by 180° by the inversion pulse 13. Depending on the time interval 14, this inversion weighting is then still present with more or less strength. If the T1 relaxation of the magnetization should simply be scanned, it is suggested to set the time interval 14 more or less to zero and to correspondingly scan the relaxation of the magnetization with the image data acquisition module 12. Given selection of the respective correct time interval 14, however, it can also be achieved that, for example, respectively either the fat signal or the water signal (for a tissue that consists of fat and water) is minimal at a point in time of the beginning of the image data acquisition mode 12, and thus the inversion pulse 13 can also be used for fat saturation or water saturation. The magnitude of the time interval is dependent on the strength of the basic magnetic field and in principle is already known.

At this point, however, other modules—for example for T2, diffusion, flow or other preparation—can be conducted. These are not shown in detail since they are sufficiently known to the man skilled in the art.

Figure 4:
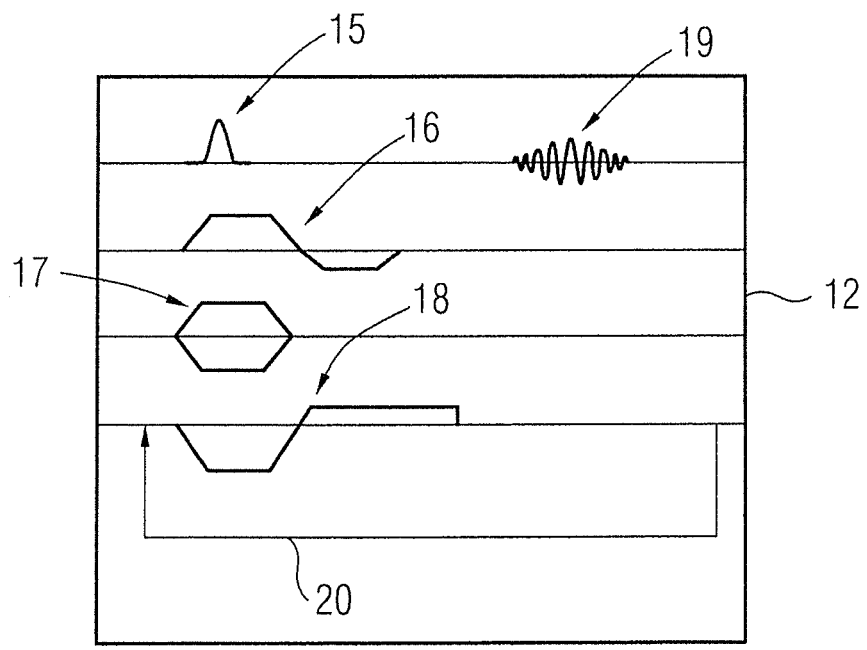
FIG. 4 shows an image data acquisition module.

FIG. 4 shows (likewise only as an example) an image data acquisition module 12. Here a magnetic resonance sequence is depicted in a known manner. It consists of an excitation pulse 15, slice coding gradient 16, a phase coding gradient 17 and a readout gradient 18. The switching of the readout gradient 18 produces what is known as an echo 19 (also called a gradient echo) with which a k-space line is acquired. If the angle of the excitation pulse 15 is selected to be sufficiently small, the data acquisition of individual k-space lines can ensue very quickly in series, i.e. with intervals in the range of milliseconds. The repeated execution of this portion of the image data acquisition module 12 is indicated by the arrow 20.

Via variation of the strength of the slice coding gradient 17 during the repeated execution, multiple slices can be read out in one RR-interval 9. The phase coding gradient 17 is then hereby normally left at the same value. A variation of the phase coding gradient 17 then only ensues in the next RR-interval 9, meaning that corresponding k-space lines of multiple images that are acquired in the different slices are respectively acquired in one RR-interval 9. However, it is also possible to first vary the phase coding gradient 17 multiple times in one RR interval 9 before the slice coding gradient 16 is changed. Multiple k-space lines of a single image data set of a specific slice can thereby be acquired, and these for multiple image data sets or corresponding slices in one RR-interval 9. An arbitrary interleaving corresponding to the changes to the gradients 16 through 18 is possible.

Figure 5:
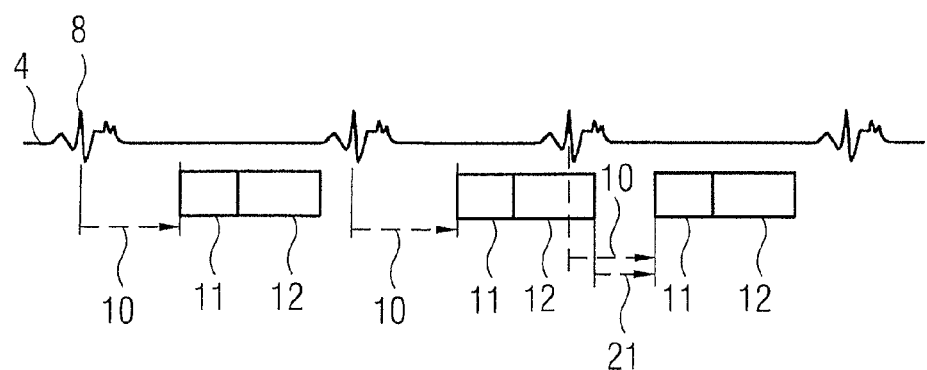
FIG. 5 shows EKG-triggered implementation of a measurement with wait time shortening.

FIG. 5 shows a method according to the invention. In this the R-spike 8 from the EKG device 6 is polled independent of the implementation of a partial measurement, in contrast to known methods. After the complete execution of the image data acquisition module 12, the control device 7 polls the occurrence of an R-spike (or a different trigger signal) in the EKG device 6 during the partial measurement. The RR-interval that is determined from the R-spike 8 before the partial measurement and the R-spike 8 during the partial measurement must hereby exceed a certain threshold. Otherwise an incorrect triggering or an arrhythmia of the heart beat is assumed. If the threshold is exceeded, the wait time 21 between the end of the image data acquisition module 12 of the last partial measurement and the preparation module 11 of the next partial measurement is chosen to be smaller than the otherwise typical time interval 10. This results in no RR-interval 9 being omitted. The actual duration of the measurement is thereby shortened.

For additional facilitation for the user it is provided that the duration of the image data acquisition module 12 is adapted to the shortened RR-interval. The points in time of the occurrence of the last four R-spikes 8 are hereby taken into account. If it is established that the successive RR-intervals 9 that are formed by the R-spikes 8 are growing increasingly shorter, the number of image data sets or, respectively, k-space lines to be acquired during the image data acquisition module 12 is reduced. This simplifies the work for the user with regard to being able to set an arbitrarily high number of image data sets to be acquired, the number of which is automatically adapted in the course of the measurement. It is thereby avoided that the user must still hectically adapt the number of image data sets to be acquired to the current heart frequency just before the beginning of the measurement. This is particularly advantageous when an acceleration of the heart beat or reduction of the heart frequency must be taken into account (for example due to an administration of medicine), wherein the resulting heart frequency cannot be precisely predicted.

In order to prevent that the number of required image data sets falls below a mandatory necessary minimum measure, the user provides a minimum number of image data sets to be acquired.

Figure 6:
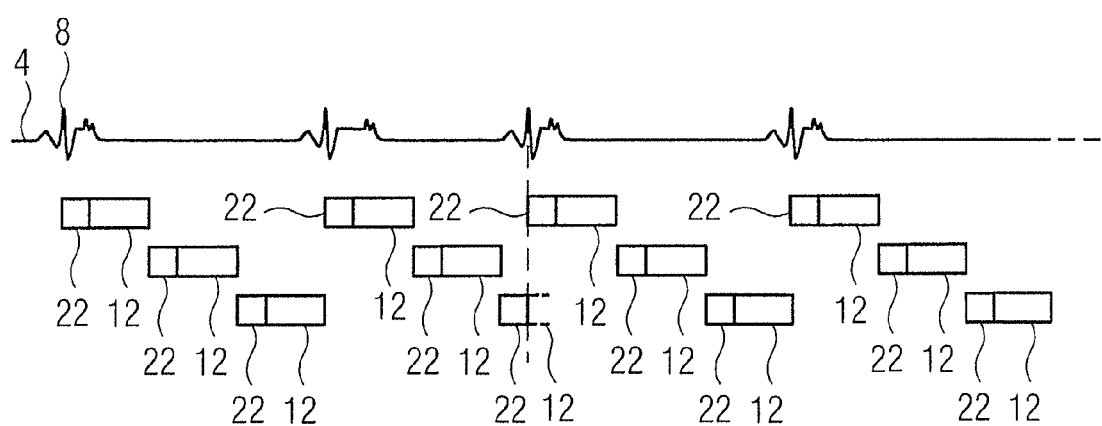
FIG. 6 illustrates the implementation of an EKG-triggered measurement with partial measurement termination.

FIG. 6 shows the acquisition of perfusion image data sets with an alternative method according to the invention. A preparation of the magnetization by means of the perfusion preparation module 22 occurs relative to the slice; a complete image data set of the respective slice is accordingly acquired in the image data acquisition module 12. As soon as the control device 7 receives the corresponding trigger signal from the EKG device 6, a partial measurement is begun by starting the first perfusion preparation module 22. If the EKG device 6 now detects an R-spike 8 during a partial measurement, no wait time 21 is available to be shortened. Another procedure is accordingly necessary. For this purpose, the data acquisition of the current image data set—thus of the image data acquisition module 12 that is used during the occurrence of the R-spike 8—is still ended. This is also the case if the R-spike 8 occurs during the perfusion preparation module 22 that precedes the image data acquisition module 12. Alternatively, the perfusion preparation module 22 or the image data acquisition module 12 could be ended immediately.

In order to ensure a specific number of image data sets, the user designates a minimum number of slices to be acquired, and therefore also image data sets. It is therefore ensured that a number of image data sets that is deemed necessary for result analysis are acquired.

In this case it is also provided to adapt the number of image data sets to be acquired depending on the points in time of the last four R-spikes 8. This cannot fall below the minimum number of image data sets to be acquired, but the user can predetermine an arbitrarily high number of slices or, respectively, image data sets to be acquired before the beginning of the measurement; this is then automatically adapted by the control device 7 within the scope of the measurement.

In both the method shown in FIG. 5 and the method according to FIG. 6, image data sets can be created whose k-space lines have not been entirely acquired. In a perfusion measurement, data sets that were acquired within the scope of morphological acquisitions can serve as reference data sets, for example. Alternatively, k-space lines can also be supplemented with the image data sets from other slices. Corresponding methods—for example GRAPPA (Generalized Autocalibrating Partially Parallel Acquisitions)—are sufficiently known.

With regard to the preparation modules 11 or perfusion preparation modules 22, it is still to be established that arbitrarily many preparation modules 11 or perfusion preparation modules 22 and image data acquisition modules 12 can alternative within the scope of a partial measurement. The EKG-triggering of the measurement is not dependent on a specific number or a specific sequence of preparation and image data acquisition cycles. The described sequences are thus merely examples and are not to be understood as limiting in any way.

Through these methods the number of unused cardiac cycles can be minimized, the number of image data sets to be acquired is automatically adapted (whereby an adjustment on the part of the user is superfluous), and the measurement time can likewise be minimized. Furthermore, artifacts can be minimized since a steady state of the magnetization can be maintained.

Although the EKG-triggering was presented in detail, the method according to the invention can be used with any type of triggering. In particular, the methods can be executed entirely analogously with triggering on breathing movement.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for triggered acquisition of magnetic resonance data in a magnetic resonance tomography apparatus, comprising the steps of:

from a control unit, operating a magnetic resonance tomography apparatus, in which an examination subject exhibiting naturally occurring, substantially periodic movement is located, to acquire magnetic resonance data forming at least one image data set, by implementing a plurality of partial data acquisitions in succession, each data acquisition resulting in acquisition of a respective segment of said at least one image data set;

detecting, via said control device, a reference point in time of a movement phase of said movement of the examination subject independently of each partial data acquisition and, from said control unit, automatically triggering the respective partial data acquisitions using said reference point in time, with a wait time having a duration between an end of each partial data acquisition and a beginning of a next partial data acquisition; and in said control unit, automatically adapting said duration of said wait time to the point in time at which said reference point in time is detected.

2. A method as claimed in claim 1 comprising acquiring magnetic resonance data from said examination subject comprising at least two image data sets.

3. A method as claimed in claim 2 comprising selecting a number of said image data sets to be acquired from the examination subject dependent on a time interval between at least two most recently detected reference points in time.

4. A method as claimed in claim 2 wherein said adapting of the wait time results in data, which would otherwise be acquired in an absence of adapting the time interval, not to be acquired, and supplementing said at least two image data sets with data from at least one reference image data set.

5. A method as claimed in claim 1 comprising, from said control device, skipping triggering of a partial data acquisition at a currently-detected reference point in time when a time interval between said currently-detected reference point in time and a detected reference point in time immediately preceding said currently-detected reference point in time, is below a predetermined threshold.

6. A method as claimed in claim 1 comprising, from said control device, detecting an EKG signal of the examination subject and using a point in time in the cardiac phase represented by said EKG signal as said reference point in time.

7. A method as claimed in claim 6 comprising using occurrence of the R-spike in said cardiac phase as said reference point in time.

8. A method as claimed in claim 1 comprising detecting a signal representing respiration of the examination subject and using a point in time in the respiration cycle represented by said respiration signal as said reference point in time.

9. A method for triggered acquisition of magnetic resonance data in a magnetic resonance tomography apparatus, comprising the steps of:

from a control unit, operating a magnetic resonance tomography apparatus, in which an examination subject exhibiting a naturally occurring, substantially periodic physiological movement is located, to acquire at least two image data sets by implementing a plurality of partial data acquisitions in succession, said at least two image data sets respectively representing different portions of the examination subject;

from said at least two image data sets, determining at least one item of perfusion information;

from said control device, detecting, independently of said partial data acquisitions, a reference point in time in a movement phase of the movement of the examination subject and triggering the respective partial data acquisitions at said reference point in time; and from said control device, automatically terminating any partial data acquisition upon detection of said reference point in time before an end of that partial data acquisition, after a predetermined time span following detection of said reference point in time.

10. A method as claimed in claim 9 comprising setting said time span to a value of zero.

11. A method as claimed in claim 10 comprising, in said control device, automatically determining said time span dependent on an end of the partial data acquisition acquired during detection of said reference point in time.

12. A method as claimed in claim 10 comprising, in said control device, automatically determining said time span dependent on complete data acquisition of a predetermined number of image data sets.

13. A method as claimed in claim 5 comprising starting detection of said reference point in time from said control device after a time duration following beginning of each partial data acquisition.

14. A method as claimed in claim 13 comprising, in said control device, determining said time duration dependent on an end of complete data acquisition of a predetermined number of image data sets.

15. A method as claimed in claim 9 comprising, in said control device, automatically determining a number of image data sets to be acquired dependent on a time interval between at least two most recently detected reference points in time.

16. A method as claimed in claim 15 comprising acquiring said number of image data sets while maintaining a minimum value for said time interval.

17. A method as claimed in claim 15 wherein an image data set is not acquired due to said threshold not being maintained, and supplementing partial data acquisitions forming said at least two image data sets with data from at least one reference image data set.

18. A method as claimed in claim 9 comprising, from said control device, skipping triggering of a partial data acquisition at a currently-detected reference point in time when a time interval between said currently-detected reference point in time and a detected reference point in time immediately preceding said currently-detected reference point in time, is below a predetermined threshold.

19. A method as claimed in claim 9 comprising, from said control device, detecting an EKG signal of the examination subject and using a point in time in the cardiac phase represented by said EKG signal as said reference point in time.

20. A method as claimed in claim 19 comprising using occurrence of the R-spike in said cardiac phase as said reference point in time.

21. A method as claimed in claim 9 comprising detecting a signal representing respiration of the examination subject and using a point in time in the respiration cycle represented by said respiration signal as said reference point in time.

22. A magnetic resonance tomography apparatus comprising:

a magnetic resonance data acquisition unit;

a control unit configured to operate said data acquisition unit, in which an examination subject exhibiting naturally occurring, substantially periodic movement is located, to acquire magnetic resonance data forming at least one image data set, by implementing a plurality of partial data acquisitions in succession, each data acquisition resulting in acquisition of a respective segment of said at least one image data set;

said control device being configured to detect a reference point in time of a movement phase of said movement of the examination subject independently of each partial data acquisition and to automatically trigger the respective partial data acquisitions using said reference point in time, with a wait time having a duration between an end of each partial data acquisition and a beginning of a next partial data acquisition; and said control unit being configured to automatically adapt said duration of said wait time to the point in time at which said reference point in time is detected.

23. A magnetic resonance tomography apparatus comprising:

a magnetic resonance data acquisition unit;

a control unit configured to operate said data acquisition unit, in which an examination subject exhibiting a naturally occurring, substantially periodic physiological movement is located, to acquire at least two image data sets by implementing a plurality of partial data acquisitions in succession, said at least two image data sets respectively representing different portions of the examination subject;

said control device being configured to determine at least one item of perfusion information from said at least two image data sets;

said control device being configured to detect, independently of said partial data acquisitions, a reference point in time in a movement phase of the movement of the examination subject and triggering the respective partial data acquisitions at said reference point in time; and said control device being configured to automatically terminate any partial data acquisition upon detection of said reference point in time before an end of that partial data acquisition, after a predetermined time span following detection of said reference point in time.

* * * * *